US007570055B1

(12) United States Patent
Clougherty et al.

(10) Patent No.: US 7,570,055 B1
(45) Date of Patent: Aug. 4, 2009

(54) MOLECULAR IDENTIFICATION AND ELECTRON RESONANCE SYSTEM AND METHOD

(75) Inventors: Dennis P. Clougherty, South Burlington, VT (US); Mark E. Eberhart, Denver, CO (US)

(73) Assignee: The University of Vermont and State Agricultural College, Burlington, VT (US)

( * ) Notice: Subject to any disclaimer, the term of this patent is extended or adjusted under 35 U.S.C. 154(b) by 65 days.

(21) Appl. No.: 11/689,497

(22) Filed: Mar. 21, 2007

Related U.S. Application Data

(60) Provisional application No. 60/784,819, filed on Mar. 21, 2006.

(51) Int. Cl.
*G01V 3/00* (2006.01)
(52) U.S. Cl. ..................................................... 324/316
(58) Field of Classification Search .......... 324/300–322
See application file for complete search history.

(56) References Cited

U.S. PATENT DOCUMENTS

| | | | | |
|---|---|---|---|---|
| 3,974,390 A | * | 8/1976 | Morita et al. ................ | 376/190 |
| 6,026,422 A | * | 2/2000 | Yamada et al. ............... | 708/523 |
| 6,141,479 A | * | 10/2000 | Heo et al. .................... | 385/141 |

OTHER PUBLICATIONS

Robert C. Atkins, Organic Chemistry A Brief Course, McGraw-Hill Publishing Co., pp. 12-13.*
Notes: "Trochoidal Electron Monochromator," by A. Stamatovic and G.J.Schulz. The Review of Scientific Instruments, vol. 39, No. 11, Nov. 1968, pp. 1752-1753.
"Excitation of Vibrational Modes Near Threshold In CO2 and N2O," by A. Stamatovic and G.J. Schulz. Physical Review, vol. 188, No. 1, Dec. 5, 1969, pp. 213-216.
Negative Ion Formation In CF2Cl2, CF3Cl and CFCl3 Following Low-Energy (0-10 eV) Impact With Near Monoenergetic Electrons, by E. Illenberger, H.U. Scheunemann and H. Baumgartel. Chemical Physics 37 (1979), pp. 21-31.
"Low Energy Electron Impact on Benzene and the Fluorobenzenes—Formation and Dissociation of Negative Ions," by Heinz-Peter Fenzlaff and Eugen Illenberger. ScienceDirect—International Journal of Mass Spectrometry and Ion Processes, vol. 59, Issue 2, Jun. 1984, pp. 185-202.
"Application of a Trochoidal Electron Monochromator/Mass Spectrometer System to the Study of Environmental Chemicals," by J.A. Laramee, C.A. Kocher, and M.L. Deinzer. Analytical Chemistry, vol. 64, No. 20, Oct. 15, 1992, pp. 2316-2322.

(Continued)

*Primary Examiner*—Brij B. Shrivastav
*Assistant Examiner*—Dixomara Vargas
(74) *Attorney, Agent, or Firm*—Downs Rachlin Martin PLLC

(57) ABSTRACT

A method of calculating an electron resonance spectra data value for each of one or more chemical constituents. In one embodiment, one or more potential electron capture orbitals is identified for each of the one or more chemical constituents; an electron orbital wavefunction is determined for each of the one or more potential electron capture Orbitals; and a theoretical electron resonance spectra data value is generated for each of the one or more chemical constituents. In another embodiment, a theoretical electron resonance spectra data value may be used to identify an unknown chemical constituent.

29 Claims, 10 Drawing Sheets

OTHER PUBLICATIONS

"Electron Monochromator-Mass Spectrometer Instrument For Negative Ion Analysis of Electronegative Compounds," by J.A. Laramee, P. Mazurkiewicz, V. Barkout, and M.L. Deinzer. Mass Spectrometry Reviews, 1996, pp. 15-42.

"Photoelectron Resonance Capture Ionization Mass Spectrometry: A Soft Ionization Source For Mass Spectrometry of Particle-Phase Organic Compounds," by Brian W. LaFranchi, James Zahardis and Giuseppe A. Petrucci. Rapid Communications In Mass Spectrometry, 2004, vol. 18, pp. 2517-2521.

"Photoelectron Resonance Capture Ionization (PERCI): A Novel Technique for the Soft-Ionization of Organic Compounds," by Brian W. LaFranchi and Giuseppe A. Petrucci. 2004 American Society for Mass Spectrometry, vol. 15, pp. 424-430.

Analysis of Nitrated Polycyclic Aromatic Hydrocarbons Using Electron Monochromator Mass Spectrometry (EM-MS), by Kent J. Voorhees, Mark E. Eberhart, Robert McCormick and Robert B. Cody. Proceedings of the 49th ASMS Conference on Mass Spectrometry and Allied Topics, Chicago, Illinois, May 27-31, 2001.

Abstract of "Comparison of Nitro-Polycyclic Aromatic Hydrocarbon Levels In Conventional Diesel and Alternative Diesel Fuels," by Cyrstal D. Havey, R. Robert Hayes, Robert L. McCormick, and Kent J. Voorhees. The 229th ACS National Meeting, San Diego, CA, Mar. 13-17, 2005.

"Capillary Gas Chromatographic Introduction of Environmental Compounds Into A Trochoidal Electron Monochromator/Mass Spectrometer," by James A. Laramee and Max L. Deinzer. Analytical Chemistry, vol. 66, No. 5, Mar. 1, 1994, pp. 719-724.

"Towards An Order-N DFT Method," by C. Fonseca, J.G. Snijders, G. te Velde, E.J. Baerends. Theoretical Chemistry Accounts (1998), vol. 99, pp. 391-403.

"Atoms, Molecules, Solids , and Surfaces: Applications of the Generalized Gradient Approximation for Exchange and Correlation," by John P. Perdew, J.A. Chevary, S.H. Vosko, Koblar A. Jackson, Mark R. Pederson, D.J. Singh and Carlos Fiolhais. Physical Review B, vol. 46, No. 11, Sep. 15, 1992, pp. 6671-6687.

"Note on Rearrangement Collisions," by T.B. Day, L.S. Rodberg, G.A. Snow, and J. Sucher. Physical Review, vol. 123, No. 3, Aug. 1, 1961, pp. 1051-1053.

* cited by examiner

MOLECULAR IDENTIFICATION AND ELECTRON RESONANCE SYSTEM AND METHOD

RELATED APPLICATION DATA

This application claims the benefit of priority of U.S. Provisional Patent Application Ser. No. 60/784,819, filed Mar. 21, 2006, and titled "Electron Resonance Spectroscopy by First-Principles," which is incorporated by reference herein in its entirety.

FIELD OF THE INVENTION

The present invention generally relates to the field of molecular identification. In particular, the present invention is directed to a molecular identification and electron resonance system and method.

BACKGROUND

Developing analytical instrumentation with high detection sensitivity and selectivity is crucial to our abilities to solve meaningful analytical problems. Among the more sensitive analytical techniques are those employing gas chromatography/mass spectrometric analysis (GC/MS), where GC-retention time, mass, and intensity are molecule selective, and therefore useful for molecular identification. For a number of years, researchers have sought to expand on MS detection methods by using a monochromatic electron beam of varying energy to scan an unknown analyte. In a process called dissociative electron capture, electrons of specific energies are captured to produce ions of characteristic masses that can be detected as a fragment ion with MS. In effect, the resonance energy spectrum—ion yield as a function of electron energy—creates an additional molecular characteristic to supplement those produced with traditional GC/MS.

An electron monochromator (EM) may be coupled to a mass spectrometer (MS) to create an EM-MS analytical tool for the investigation of electrophilic compounds. For example, an EM-MS may provide a powerful tool for molecular identification of compounds contained in complex matrices, such as environmental samples. However, before this tool can realize its full potential, it will be necessary to create a library of resonance energy scans from standards of the molecules for which EM-MS offers a practical means of detection. Unfortunately, the number of such standards is very large and not all of the compounds are commercially available, making this library difficult to construct.

SUMMARY OF THE DISCLOSURE

In one embodiment, a method of calculating an electron resonance spectra data value for each of one or more chemical constituents is provided. The method includes identifying one or more potential electron capture orbitals for each of the one or more chemical constituents; determining an electron orbital wavefunction for each of the one or more potential electron capture orbitals; and generating a theoretical electron resonance spectra data value for each of the one or more chemical constituents from the corresponding electron orbital wavefunctions.

In another embodiment, a computer readable medium containing computer executable instructions implementing a method of calculating an electron resonance spectra data value for each of one or more chemical constituents is provided. The instructions include a set of instructions for identifying one or more potential electron capture orbitals for each of the one or more chemical constituents; a set of instructions for determining an electron orbital wavefunction for each of the one or more potential electron capture orbitals; and a set of instructions for generating a theoretical electron resonance spectra data value for each of the one or more chemical constituents from the corresponding electron orbital wavefunctions.

In yet another embodiment, a system for calculating an electron resonance spectra data value for each of one or more chemical constituents is provided. The system includes means for identifying one or more potential electron capture orbitals for each of the one or more chemical constituents; means for determining an electron orbital wavefunction for each of the one or more potential electron capture orbitals; and means for generating a theoretical electron resonance spectra data value for each of the one or more chemical constituents from the corresponding electron orbital wavefunctions.

In still another embodiment, a method for modeling isomeric differentiation in molecular identification of one or more chemical constituents is provided. The method includes identifying one or more potential electron capture orbitals for each of a plurality of isomers of the one or more chemical constituents; determining an electron orbital wavefunction for each of the one or more potential electron capture orbitals; generating a theoretical electron resonance spectra data value for each of the plurality of isomers from the corresponding electron orbital wavefunctions; and comparing a measured electron resonance spectra data value for an unknown isomer with the theoretical electron resonance spectra data values for the plurality of isomers to identify the unknown isomer.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
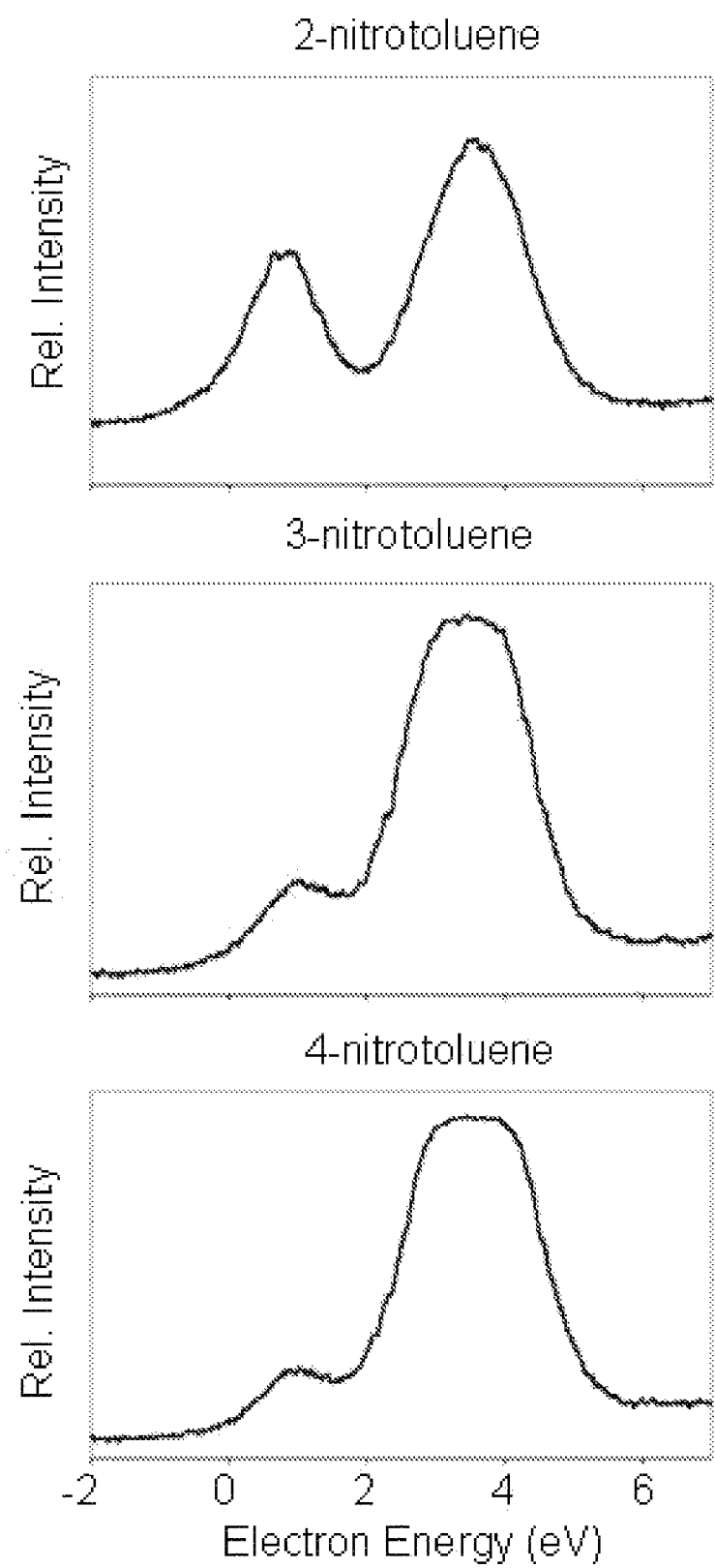
FIG. 1 illustrates examples of ion yield curves for m/z 46 as a function of electron energy for three isomers of mononitrotoluene obtained by electron monochromator-mass spectrometry.

In dissociative electron capture, as well as other ionization analytical techniques, fragmentation of a chemical constituent (e.g., an unknown analyte) may be useful for identifying and/or determining one or more characteristics of the chemical constituent. For example, in EM-MS an electron of a specific energy may be captured by a molecule of a chemical constituent to produce an ion of a characteristic mass that may be detected as a fragment ion. Equation (1) below illustrates one example of such an electron capture:

$$e^- + AB \rightarrow A^{\cdot} + B^- \quad (1)$$

where AB is an isomer of a chemical constituent, B is a negatively charged fragment, and A· is a radical. In one embodiment, a theoretical electron resonance spectra data may be calculated for a chemical constituent subjected to electron capture, such as that in equation (1). Electron resonance spectra data includes spectrographic data predicted to exist for a given chemical constituent. The term theoretical is used herein to distinguish between data that is calculated and data that is obtained experimentally. Such data may be determined without subjecting a sample of the chemical constituent to an actual spectroscopic analysis. Example electron resonance spectra data include, but are not limited to, a fragmentation probability value, a reaction rate for electron capture, an electron resonance spectrum, an electron resonance energy value, a relative electron energy peak intensity value, an electron energy peak width, and any combinations thereof. In another embodiment, a rate of reaction for an electron capture, such as that in equation (1), may be calculated to determine probability of fragmentation and/or an approximation of an electron capture resonance spectra data for the chemical constituent. In yet another embodiment, theoretical electron resonance spectra data (e.g., an approximation of a probability of fragmentation and/or an electron capture resonance spectrum) may be utilized to identify an unknown chemical constituent by an experimentally obtained property (e.g., an experimentally obtained electron capture resonance spectrum for the unknown chemical constituent). In one example, such approximations may be utilized to identify individual isomers of a chemical constituent.

An experimentally obtained electron resonance spectra data (e.g., an electron resonance spectrum) may include spectrographic data from an analytical analysis of a chemical constituent (e.g., a spectral analysis using an EM-MS technique). In one example, an electron resonance spectrum may include the ion yield as a function of electron energies. In such an example, an electron resonance spectrum may be referred to as an ion yield curve. As described in more detail below, a theoretical or approximation of an electron resonance spectrum may be calculated for a chemical constituent for use in comparing with experimental data for identifying chemical constituents. The following discussion of experimental spectrographic data may assist in understanding the theoretical approximations of fragmentation rates and/or electron resonance spectra described below.

Table 1 illustrates exemplary experimental spectral data for various nitrated aromatic compounds. The exemplary spectral data (including energies and relative intensities of both the electron-capture resonances typical of nitrated aromatic groups) was obtained using a trochoidal electron monochromator interfaced to an MStation JMS 700-T four sector mass spectrometer, each available from JOEL USA, Inc. of Peabody, Mass. The filament potential, with respect to its center, was scanned from −3 to 12 eV with an electron current of 20 uA. The energy resolution was +0.4 eV. A 6.0 kV accelerating voltage was used, the resolution was set to 1000, and the EM source temperature was 280° C. The electron energy scale was calibrated using nitrobenzene and hexafluorobenzene standards (diluted or dissolved into toluene, ChromAR grade available from Mallinckrodt Chemicals of Phillipsburg, N.J., at a concentration of 100 ng/μL) introduced to the ionization source via a heated reservoir. The molecular ion of nitrobenzene (m/z 123) was assigned a resonance energy value of 0.06 eV, while the first and second $NO_2^-$ (m/z 46) resonance peaks were assigned values of 1.2 eV and 3.5 eV, respectively. For hexafluorobenzene, the molecular ion (m/z 186) was assigned a value of 0.03 eV, while the first and second m/z 167 peaks from the $C_6H_5^-$ fragment were assigned 4.5 eV and 8.3 eV, respectively. One microliter of each sample solution was injected onto an HP 6890 Series GC equipped with an on-column injector port to avoid degradation of the compounds at the inlet. A 30-m ZB-5 column set to 280° C. was used for resonance energy measurements except for 1,3-dinitropyrene, in which the column temperature was set to 300° C. The electron energy scans were carried out using a JEOL electron monochromator power supply modified with an energy sweep board. A Tektronix (Beaverton, OR) TDS2022 two-channel oscilloscope interfaced to the JEOL NIR Energy Sweep Utility program was used for data acquisition.

TABLE 1

Resonance Energies for m/z 46 anions of nitro aromatic compounds (bond type: C—NO₂).

| Compound | Resonance Energy (eV) | Normalized Relative Intensities (%) | Compound | Resonance Energy (eV) | Normalized Relative Intensities (%) |
|---|---|---|---|---|---|
| 2-nitrotoluene | 0.8, 3.6 | 60, 100 | 2-nitrobiphenyl | 1.0, 4.0 | 100, 89 |
| 3-nitrotoluene | 1.0, 3.5 | 26, 100 | 3-nitrobiphenyl | 1.1, 3.9 | 23, 100 |
| 4-nitrotoluene | 1.0, 3.6 | 21, 100 | 2,2'-dinitrobiphenyl | 0.6, 4.0 | 64, 100 |

TABLE 1-continued

Resonance Energies for m/z 46 anions of nitro aromatic compounds (bond type: C—NO$_2$).

| Compound | Resonance Energy (eV) | Normalized Relative Intensities (%) | Compound | Resonance Energy (eV) | Normalized Relative Intensities (%) |
|---|---|---|---|---|---|
| 2,6-dinitrotoluene | 0.6, 3.4 | 21, 100 | 3,4'-dinitrobiphenyl | 1.0, 3.9 | 31, 100 |
| 2-nitro-m-xylene | 1.0, 4.1 | 100, 77 | 6-nitroquinoline | 1.2, 3.3 | 24, 100 |
| 4-nitro-m-xylene | 1.0, 4.0 | 39, 100 | 2-nitroanthracene | 2.7 | 100 |
| 5-nitro-m-xylene | 1.1, 3.9 | 14, 100 | 9-nitroanthracene | 1.4, 4.0 | 100, 96 |
| 2-nitrophenol | 3.5 | 100 | 9,10-dinitroanthracene | 4.7 | 100 |
| 4-nitrophenol | 1.3, 3.9 | 14, 100 | 4-nitrophenanthrene | 0.7, 3.9 | 57, 100 |
| 1-nitronaphthalene | 0.8, 3.1 | 39, 100 | 1-nitropyrene | 3.6 | 100 |
| 2-nitronaphthalene | 1.0, 3.2 | 16, 100 | 1,3-dinitropyrene | 4.0 | 100 |
| 1,3-dinitronaphthalene | 3.4 | 100 | 3-nitrofluoranthene | 2.8, 4.7 | 100, 77 |
| 1,8-dinitronaphthalene | 0.7, 3.7 | 40, 100 | | | |

FIG. 1 illustrates exemplary ion yield curves for m/z 46 as a function of electron energy for the three isomers of mononitrotoluene obtained by EM-MS. From Table 1 and FIG. 1, the exemplary electron resonance spectrum for 2-nitrotoluene includes a resonance energy peak at 0.8 electron Volts (eV) and a resonance energy peak at 3.6 eV with normalized relative intensities of 60% and 100%, respectively. The exemplary electron resonance spectrum for 3-nitrotoluene includes a resonance energy peak at 1.0 eV and a resonance energy peak at 3.5 eV with normalized relative intensities of 26% and 100%, respectively. The exemplary electron resonance spectrum for 4-nitrotoluene includes a resonance energy peak at 1.0 eV and a resonance energy peak at 3.6 eV with normalized relative intensities of 21% and 100%, respectively. Knowledge of expected electron resonance spectra and/or other electron resonance spectra data for chemical constituents can be used to identify unknown chemical constituents, including identification of isomers. As discussed above, the time and complexity of experimentally profiling electron capture data, such as that of Table 1, for all possible chemical constituents is prohibitive.

Figure 2:
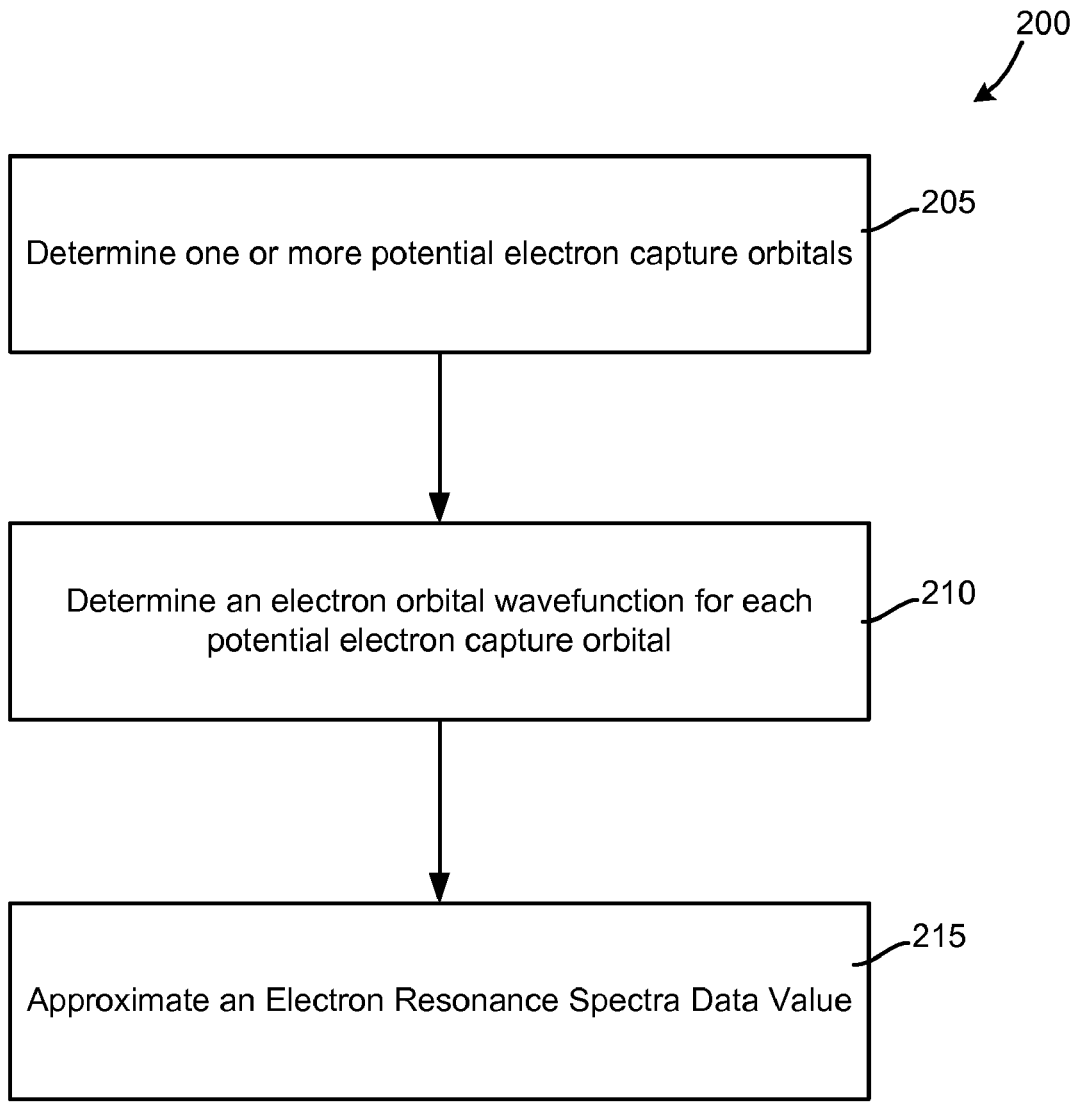
FIG. 2 illustrates one embodiment of a method for approximating a rate of reaction for electron capture for a chemical constituent.

FIG. 2 illustrates one embodiment of a method 200 for approximating a electron resonance spectral data for a chemical constituent. The approximated electron resonance spectra data (e.g., a rate of reaction and/or an electron resonance spectrum data) may be utilized to identify an unknown chemical constituent without experimentally building a profile for the particular chemical constituent. At step 205, one or more potential electron capture orbitals for the chemical constituent are determined. The one or more potential electron capture orbitals are one or more molecular orbitals of the chemical constituent that are most likely to capture the electron. In one example, one or more potential electron capture orbitals may be determined by empirical analysis of the three-dimensional molecular orbital characteristics. In another example, one or more potential electron capture orbitals may be consistent across a group of similar chemical constituents having similar structure. Such an example is discussed below with respect to the experimental data for nitrated aromatic compounds, where in one example, π-orbitals are most likely to be electron capture orbitals for nitrated aromatic compounds. In yet another example, one or more potential electron capture orbitals for a group of chemical constituents may be determined by empirical observation of actual electron resonance spectra for one or more chemical constituents of the group. One such example is discussed below with respect to FIG. 3.

At step 210, an electron orbital wavefunction is determined for each of the potential electron capture orbitals. A molecular orbital wavefunction may be determined by any of a variety of processes. In one example, a computer software based tool may be utilized to determine an orbital wavefunction. Example software tools for determining an orbital wavefunction include, but are not limited to, Gaussian, DMOL, and electronic structure code. The wavefunction used for each orbital may be a wavefunction for any state of the molecular orbital. Example molecular orbital states include, but are not limited to, a ground state and an excited state. In one example, each wavefunction may be a wavefunction for a single electron. The determination of each electron orbital wavefunction may alternatively be conducted as part of step 205 and the resultant wavefunctions also used to identify one or more potential capture orbitals (e.g., by empirical analysis of wavefunction characteristics).

At step 215, an approximation of a electron resonance spectra data is generated using the orbital wavefunctions for the one or more capture orbitals. In one example, this approximation may be determined by a process that includes performing a Fourier Transform of each of the wavefunctions of each of the potential capture orbitals. The Fourier Transforms may then be averaged over all wave vectors of the Fourier Transform while keeping the overall wave vector magnitude fixed. In another example, a reaction rate for electron capture may be calculated using equation (2):

$$\Gamma = \frac{V_0^2}{2\hbar\Omega} \int \frac{d^3\vec{K} d\Omega_k}{(2\pi)^3} |\phi(\vec{k})|^2 \delta(\varepsilon_k + \varepsilon_\phi - E_K - \Delta) \quad (2)$$

where k is an unperturbed plane wave state of an incident electron, φ(k) is a molecular orbital wavefunction, $V_0$ is a repulsive constant, $\epsilon_k$ is a kinetic energy of the incident electron, $E_K$ is a final fragment kinetic energy, $\epsilon_\phi$ is an electron binding energy for the capturing orbital, Ω is a volume of a box used to normalize the continuum eigenstates, and Δ is a binding energy of the fragment to the core. In one example, a reaction rate for electron capture may represent and/or be used to calculate a fragmentation probability value for a chemical constituent. In another example, a reaction rate for electron capture may represent and/or be used to calculate one or more electron resonance spectrum data (e.g., resonance energy, relative peak intensity, peak width).

Steps 205 to 215 may be repeated for multiple chemical constituents. The iteration of steps 205 to 215 may utilize a prior determination of potential capture orbitals (e.g., where successive chemical constituents share similar chemical structure such that predicted capture orbitals may be the same). The resultant data for one or more iterations of steps 205 to 215 may be compiled into a library of data that may be used to identify unknown chemical constituents. Such a library may also include data that has been experimentally obtained.

The approximations of spectral data may be stored and/or utilized in a variety of ways. In one example, one or more chemical constituent profiles (e.g., approximation electron resonance spectra data, such as data of electron capture reaction rate, electron resonance spectral data, probability of fragmentation) may be stored in association with a computer readable medium. Example computer readable media are discussed below with respect to an exemplary computing device (see FIG. 10). In another example, one or more chemical constituent profiles may be displayed via a display device. Example display devices are discussed below with respect to FIG. 10. In yet another example, method 200 may be implemented in conjunction with a real-time analytical data measurement in which experimental data is obtained for a chemical constituent. In such an example, one or more chemical constituent profiles may be determined according to method 200 for comparison to the experimental data. The one or more chemical constituent profiles may be for chemical constituents that are suspected as likely to be the unknown chemical constituent submitted to experimental analysis.

In another exemplary aspect, one or more chemical constituent profiles (stored or calculated at the time of analysis) may be used in conjunction with a variety of analytical techniques. Examples of analytic techniques include, but are not limited to, EM-MS, GC-EM-MS, and matrix assisted laser desorption/ionization (MALDI). In one example, comparison of experimental data with the one or more chemical constituent profiles may be used to identify an unknown chemical constituent. In another example, one or more chemical constituent profiles may be utilized to predict rates of reaction for use with a MALDI technique. In still another example, it may be possible to narrow prospective determinations for an unknown chemical constituent using a conventional analytical technique (e.g., determining a chemical compound type, but not isomer information, for an unknown chemical constituent using a technique, such as GC-MS). A technique such as EM-MS may be utilized to determine experimental electron resonance spectra data for comparison to one or more chemical constituent profiles derived from a method such as method 200. Isomeric identification may then be made via the comparison.

In one exemplary aspect, an EM-MS technique may expand the application and selectivity of traditional MS through the inclusion of a new dimension in the space of molecular characteristics—the electron resonance energy spectrum. In another exemplary aspect, EM-MS may also enhance detection sensitivity potentially by having the entire electron flux of the proper energy being delivered into the negative ion resonance that is analytically most useful to solving the a given problem.

Figure 3:
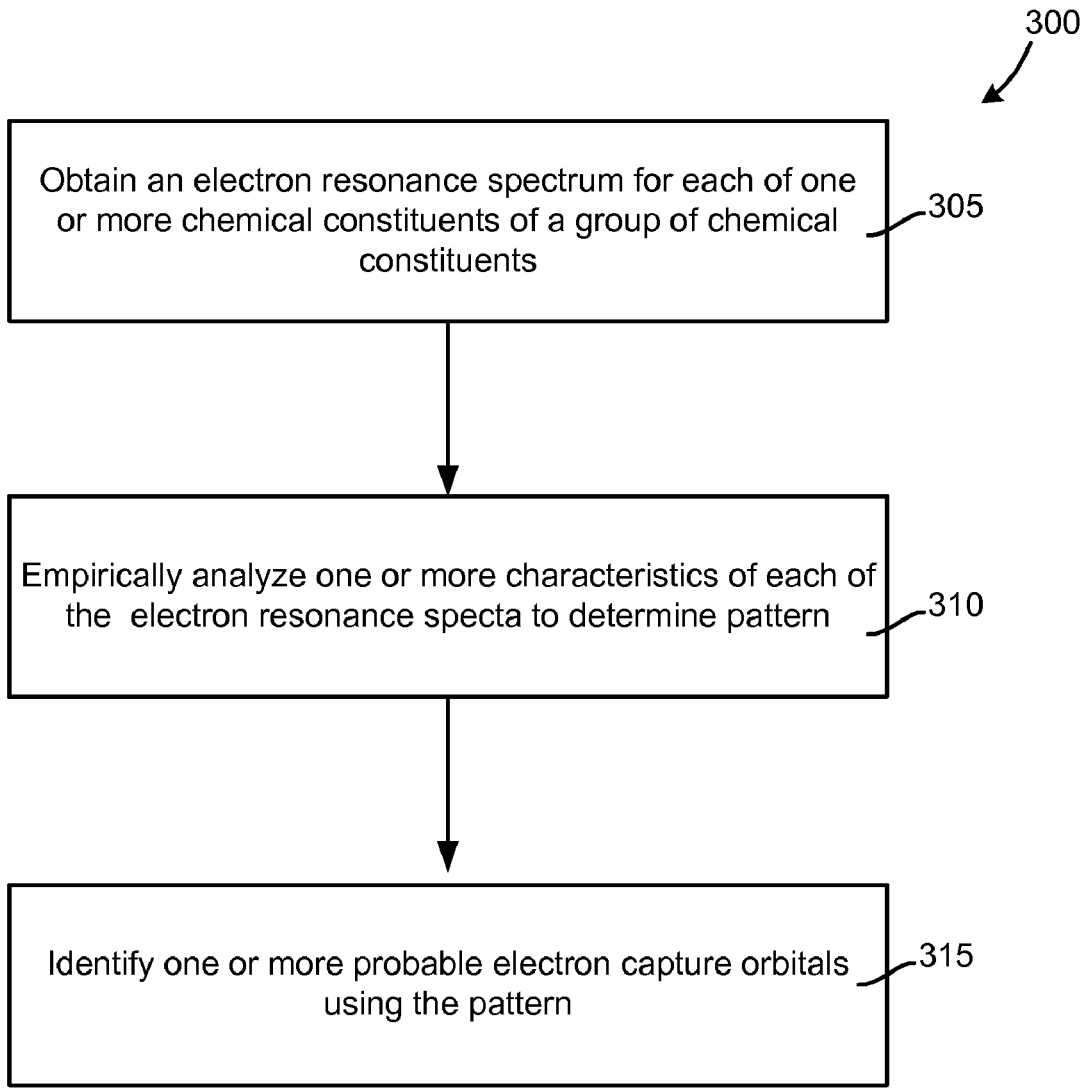
FIG. 3 illustrates one embodiment of a method for determining one or more candidate molecular orbitals for potential electron capture orbitals.
Figure 4A:
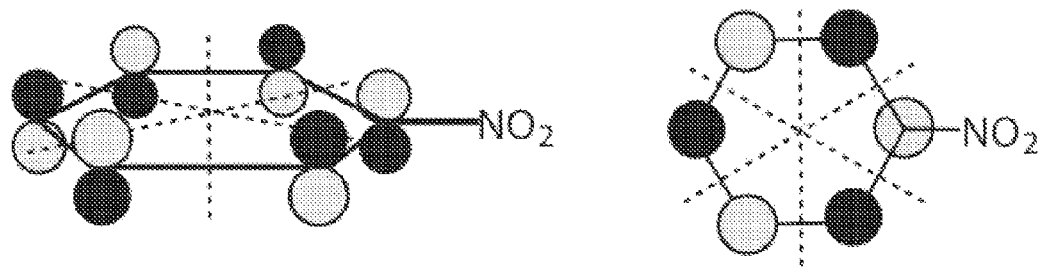
FIG. 4A illustrates one example of a depiction of an unoccupied $\pi$-orbital of an exemplary substituted phenyl compound.
Figure 4B:
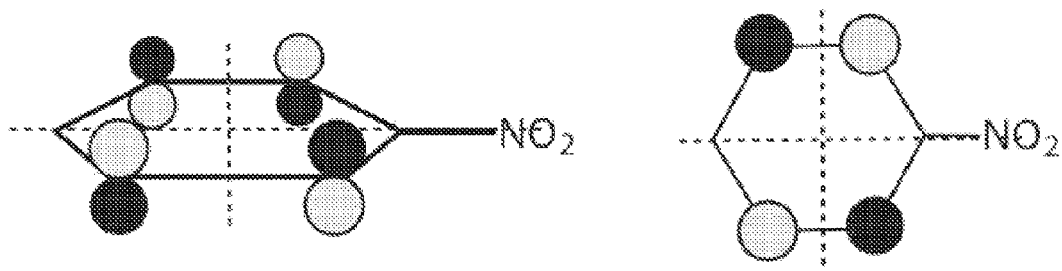
FIG. 4B illustrates one example of a depiction of a LUMO+1 for an exemplary nitro aromatic compound.
Figure 4C:
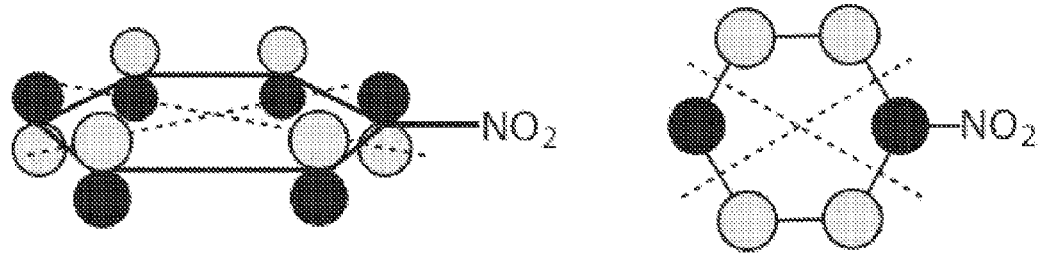
FIG. 4C illustrates one example of a depiction of a LUMO for an exemplary nitro aromatic compound.
Figure 5A:
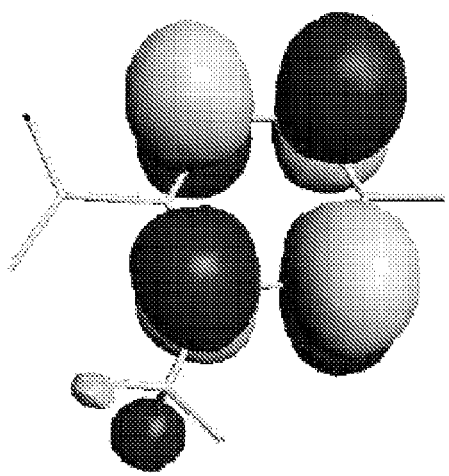
FIG. 5A illustrates one example of a depiction of a LUMO+1 for 2-nitrotoluene.
Figure 5A:
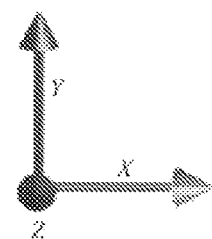
Figure 5B:
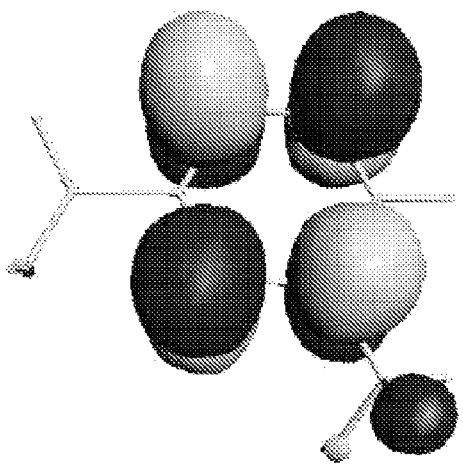
FIG. 5B illustrates one example of a depiction of a LUMO+1 for 3-nitrotoluene.
Figure 5C:
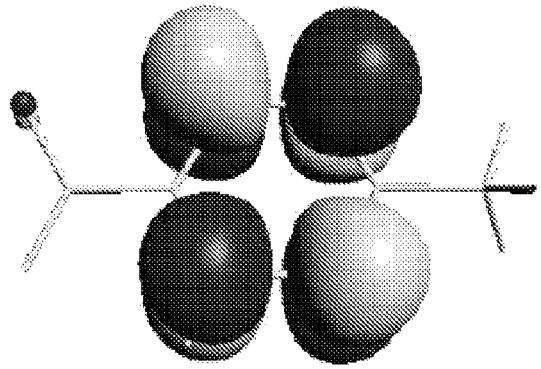
FIG. 5C illustrates one example of a depiction of a LUMO+1 for 4-nitrotoluene.

FIG. 3 illustrates one embodiment of a method 300 for determining one or more candidate molecular orbitals for potential electron capture orbitals (e.g., for use with method 200 of FIG. 2). At step 305, an electron resonance spectrum is obtained for each of one or more chemical constituents of a group of chemical constituents. In one example, the group of chemical constituents may include chemical constituents having similar structure with one or more differing functional groups. At step 310, one or more characteristics of each of the electron resonance spectra is empirically analyzed to determine one or more patterns in spectral peak shifting as a function of the variance in functional group on each of the chemical constituents. At step 315, one or more molecular orbitals are identified for the group of chemical constituents that is most likely to capture an electron by selecting those molecular orbitals where the symmetry displays the same patterns as found by step 310.

Example for Nitrated Aromatic Compounds

Yet another embodiment of identification of chemical constituents and isomers is described below with respect to FIGS. 4 to 9. The following discussion is directed to nitrated aromatic compounds, such as those set forth in Table 1. It should be noted that various aspects discussed herein may be readily applied to other chemical constituents and/or classes of chemical constituents.

In one example, isomers of nitrotoluene can be analyzed. Equation (1) may be utilized again for this analysis:

$$e^- + AB \rightarrow A \cdot + B^- \quad (1)$$

where AB is an isomer of nitrotoluene, B is a negatively charged nitro fragment, and A· is a toluene radical. The radical toluene fragment is much more massive than either the electron or the nitro fragment. Ignoring the kinetic energy of the toluene fragment the Hamiltonian can be expressed as:

$$H = T_e + T_B + V_{e-A} + V_{AB} + V_{e-B} \quad (3)$$

where $T_e$ and $T_B$ are the kinetic energies of the electron and the nitro fragment, respectively; $V_{e-A}$ and $V_{e-B}$ are the interactions of the electron with the toluene and the nitro fragments, respectively; and $V_{AB}$ is the interaction of the nitro group and the toluene fragment.

The toluene fragment may be identified to be a massive "core." The interactions with the core fragment may be eliminated from the transition matrix (T-matrix) element. In the first-order Born approximation, the T-matrix element is given by, $$\langle A^-, B|T|e^-, AB \rangle = \langle \phi, \vec{K} | V_{e-B} | \vec{k}, \Phi_b \rangle \quad (4)$$

where $|\vec{k}\rangle$ is the unperturbed plane wave state of the incident electron, $|\phi\rangle$ is the molecular orbital of the core that captures the electron, $|\Phi_b\rangle$ is the bound state of the nitro fragment to the core, and $|\vec{K}\rangle$ is the plane wave state of the detached nitro fragment.

With the nitro fragment so deeply bound to the toluene core, initially the further approximation is made that $\langle \vec{R} | \Phi_b \rangle \approx \delta(R)$, giving $$\langle A^-, B|T|e^-, AB \rangle \approx \frac{1}{\sqrt{\Omega}} \langle \phi | V_{e-B} | \vec{k} \rangle \quad (5)$$

where Ω is the volume of the box used to normalize the continuum eigenstates.

Lastly, it is recognized, on the basis of ab-initio density functional calculations on nitrotoluene, that the incoming electron is attracted to the phenyl moiety and repelled by the nitro group because a permanent dipole is present in this class of chemical compounds. Such an interaction is long-range, and over the extent of the short-range bound state in which the electron is captured, the electron-nitro interaction can be approximated as a repulsive constant $V_{e-B} \approx V_0$.

$$\langle A^-, B|T|e^-, AB\rangle \approx \frac{V_0}{\Omega} \int d^3\vec{r} e^{i\vec{k}\cdot\vec{r}} \phi_*(\vec{r}) \equiv \frac{V_0}{\Omega} \phi_*(\vec{k}) \qquad (6)$$

By Fermi's Golden Rule, the reaction rate of Equation (1) averaged over all molecular orientations—a quantity closely related to the electron capture resonance spectra-is given by, $$\Gamma = \frac{V_0^2}{2\hbar\Omega} \int \frac{d^3\vec{K}d\Omega_k}{(2\pi)^3} |\phi(\vec{k})|^2 \delta(\varepsilon_k + \varepsilon_\phi - E_K - \Delta) \qquad (7)$$

where $\epsilon_k$ is the incident electron kinetic energy, $E_K$ is the final fragment kinetic energy, $\epsilon_\phi$ is the electron binding energy for the capturing orbital, and $\Delta$ is the binding energy of the nitro fragment to the toluene core. The Fourier transform of the capturing orbital is indicated as the term $\phi(k)$.

The molecular orbital into which the incident electron is initially captured may be determined in evaluating this matrix element. In one example, inspection of Table 1 suggests that in the case of nitrated aromatic compounds, attention may be restricted to the unoccupied π-orbitals. The rationale behind this conclusion derives from the observation that the resonance energies do not vary substantially among compounds characterized by strikingly different functionalities, e.g. nitrophenol and nitrotoluene, both of which show primary resonances close to 3.6 eV. Accordingly, the wavefunctions of the capturing molecular orbital are also unlikely to show appreciable variation.

In this example, the only wavefunctions that could satisfy this constraint are those of the molecular π-orbitals, which will be characterized by contributions from the $P_z$ orbitals of the nitro group and ring carbons (z can be considered to be normal to the aromatic ring). Ring functionalities without π-electrons, e.g. methyl or hydroxyl groups, will contribute only modestly to these molecular π-orbitals.

FIG. 4 illustrates three unoccupied π-orbitals of substituted phenyl compounds, like the isomers of nitrotoluene, the structure of which can be predicted from simple nodal arguments.

The lowest lying of the three molecular orbitals is the least unoccupied molecular orbital "LUMO" (see FIG. 4C) and possesses two nodal planes, neither of which contains the nucleus of a ring carbon atom. This forces the nitro-to-ring interaction to be π-bonding. The other π-orbital with two nodal planes is generally the LUMO+1 (see FIG. 4B). One of its nodal planes contains the ring carbon bound to the nitrogen atom, producing a non-bonding interaction between the nitro group and the ring. At still higher energies is the fully anti-bonding π-orbital characterized by three nodal planes (see FIG. 4A). By virtue of the placement of its nodal planes, the nitro-to-ring nonbonding orbital will be composed almost entirely of the $p_z$ atomic orbitals on the carbon atoms at the 2, 3, 5, and 6 positions relative to the nitro group. As such, it may be expected that this orbital will be nearly identical in the isomers of nitrotoluene and nitrophenol and thus is likely to be the orbital into which a 3.6 eV electron may be captured.

FIG. 5 illustrates isosurfaces for the LUMOs+1 of 2-, 3-, and 4-nitrotoluene as computed from first principles using the Amsterdam Density Functional code. See, LaFranchi, B. W.; Petrucci, G. A., *J. Am. Soc. Mass Spectrom.* 2004, 15, 424-430, which is incorporated herein in its entirety for a discussion of the Amsterdam Density Functional code. These orbitals are similar and localized on the ring, with very little amplitude on the nitro or methyl functionalities.

In this example, with a candidate capturing wavefunction, the energy of an incident electron that will maximize the matrix element $\langle \vec{k}|\psi_2\rangle$ must be determined. In this example, $|\psi_2\rangle$ is the state corresponding to the LUMO+1. This observation invites the evaluation of the matrix element through a plane wave expansion of the capturing orbital and a direct determination of its overlap with an incident electron.

Noting in this example that electron capture is governed by a "local symmetry" that may be higher than that of the full molecule, a semiquantitative analysis is possible. This local symmetry is that of the potential only on those sites where the wavefunction of the capturing molecular orbital has significant amplitude. Referring again to FIG. 5, the symmetry governing the capture of an electron into the LUMO+1 of 2-, 3-, or 4-nitrotoluene is illustrated to be that of the potential about the carbon atoms at the 2, 3, 5, and 6 ring positions relative to the nitro group. The LUMO is localized on these atoms. Over this region, the symmetry is nearly $D_{2h}$. This symmetry governs electron capture into the LUMOs+1 of the isomers of nitrotoluene. In this example and under this local symmetry, if the capturing matrix element is to be nonzero, the capturing LUMO shares the same irreducible representation as the wavefunction of the incident electron.

The LUMOs+1 of the isomers of nitrotoluene, all transform as the $A_u$ irreducible representation of the $D_{2h}$ point group. A component of a general plane wave with this symmetry can be projected. This exercise reveals the wavefunction of the incident electron to be, i $\sin(k_x x)\sin(k_y y)\sin(k_z z)$, where $k_x$, $k_y$, and $k_z$ are the Cartesian components of the electron's wavevector. Note that the wavefunction vanishes, if any of these components is zero.

Figure 6A:
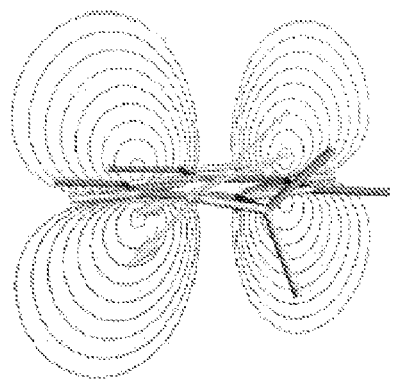
FIG. 6A illustrates one example of a projection of exemplary half-wavevectors that are 'in phase' with a LUMO+1 of 2-, 3-, and 4-nitrotoluene.
Figure 6B:
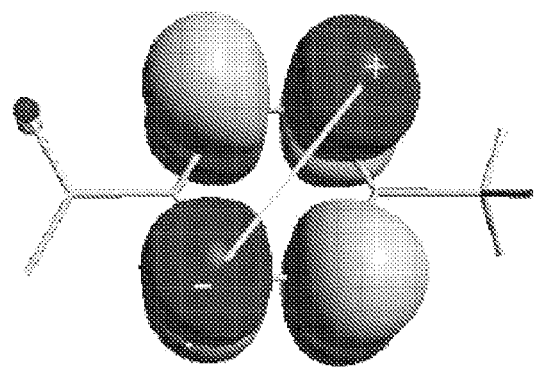
FIG. 6B illustrates another example of a projection of exemplary half-wavevectors onto an xy-plane of 4-nitrotoluene.
Figure 6B:
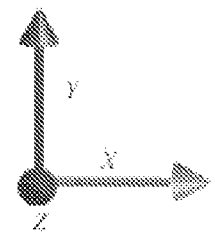
Figure 6C:
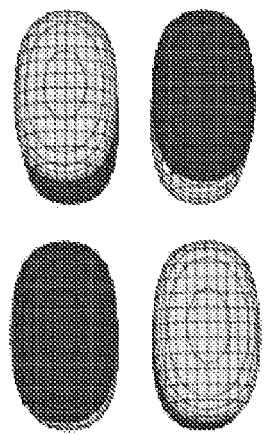
FIG. 6C illustrates one example of a wavefunction corresponding to the wavevector of FIG. 6B.

FIG. 6A illustrates exemplary half-wavevectors that are "in phase" with the LUMO+1 of 2-, 3-, and 4-nitrotoluene projected onto the plane normal to the ring and containing ring carbons 1 and 4 relative to the methyl group. FIG. 6B illustrates another example projection of this wavevector onto the xy-plane of 4-nitrotoluene. FIG. 6C illustrates a corresponding wavefunction to this wavevector. There is constructive overlap between the wavefunction and the LUMO in FIG. 6A.

The Fourier transform of the LUMO+1 has a substantial magnitude for wavevectors corresponding to a phase shift of π along a displacement vector connecting orbital lobes of opposite phase, as depicted in FIGS. 6A and 6B. The magnitude of this wavevector can be estimated by placing the endpoints of the displacement vector in the regions of highest amplitude for the orbital lobes. This displacement must be a half-wavelength to correspond to having the electron wavefunction undergo a phase change of π.

It is now possible to estimate the wavelength of the incident captured electron and hence its energy. The x-component of the displacement vectors shown in FIG. 6A corresponds to the distance between neighboring ring carbon atoms (e.g., 1.4 Angstroms (Å)). The y-component is the distance between carbon atoms meta to each other (e.g., 2.42 Å). The z-component varies from an upper limit (e.g., 2 Å) to a lower limit given by the distance between the LUMO extrema, or approximately 1 Å. These values yield electron wavelengths between 6.9 and 5.9 Å, corresponding to wavevectors between, 0.9 and 1.1 Å$^{-1}$, and electron energies between 3.2 and 4.3 eV respectively. Using these values for $k_x$, $k_y$, and $k_z$ a double isosurface for the corresponding wavefunction is shown as FIG. 6C, which, overlaps constructively over all space with the molecular wavefunction, accounting for the large amplitude of the resonance at 3.6 eV. These calculated values for electron capture data are consistent with the experimental scans show a broad electron resonance at 3.6 eV, but with a half width of nearly 1.5 eV. The approximated theoretical data is well within a reasonable margin of error, and correctly predicts the peak resonance energy. In one exemplary aspect, the model may attribute the observed width of the spectrum to the broadness of the Fourier transform of the LUMO+1 around this optimum k-value, which may be due, in part, to the slow decay of the $p_z$ atomic-wavefunctions normal to the ring.

Isomer-dependent amplitude variations of a secondary electron resonance at about 1.0 eV are studied as an application of isomeric discrimination. The energy of this resonance also varies little between isomers, again suggesting that the capturing orbital is $\pi$ in character. In one example, electron capture into the LUMO is responsible for this resonance in isomers of nitrotoluene.

Figure 7A:
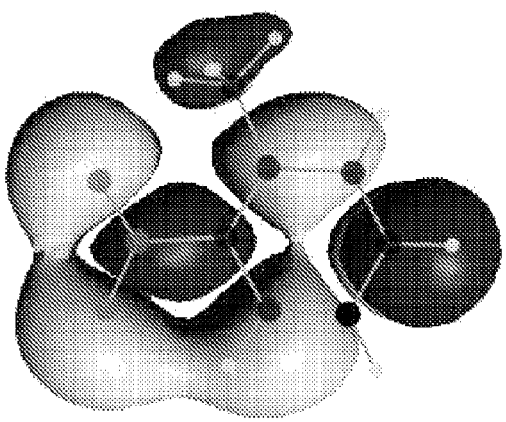
FIG. 7A illustrates another example depiction of a LUMO for 2-nitrotoluene.
Figure 7B:
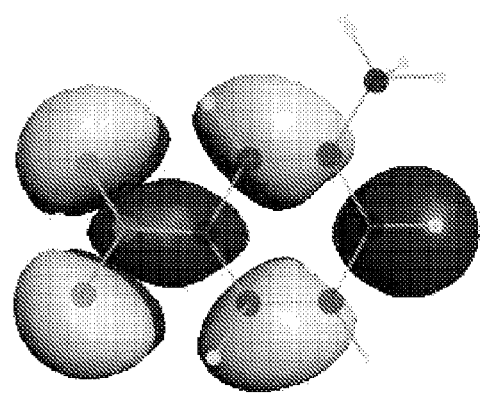
FIG. 7B illustrates another example depiction of a LUMO for 3-nitrotoluene.
Figure 7C:
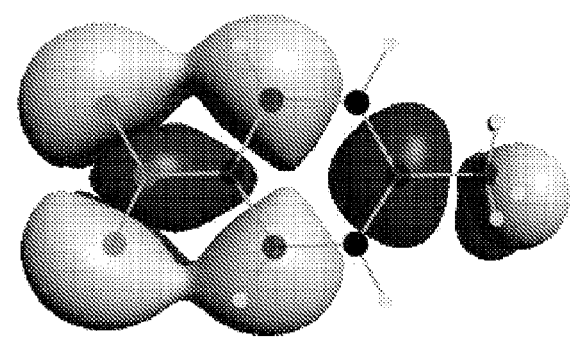
FIG. 7C illustrates another example depiction of a LUMO for 4-nitrotoluene.

FIG. 7A illustrates LUMOs of 2-nitrotoluene. FIG. 7B illustrates LUMOs of 3-nitrotoluene. FIG. 7C illustrates LUMOs of 4-nitrotoluene. Similarity exists between the molecular orbitals of 3- and 4-nitrotoluene. The local symmetry of 3-nitrotoluene and 4-nitrotoluene are approximately $C_2V$ by virtue of a near reflection symmetry in the plane normal to the ring containing the carbon to nitrogen bond. However, 2-nitrotoluene has an asymmetric LUMO because of significant wave amplitude on the methyl group, reducing the local symmetry to $C_h$. This difference may lead to the larger secondary resonance intensity of 2-nitrotoluene compared to the other two isomers (see FIG. 1).

Under the local $C_{2v}$ symmetry, the LUMOs of 3- and 4-nitrotoluene reduce as $B_1$. Projecting this component from a general plane wave gives the wavefunction of the incident electron to be, $$\phi(k_x,k_y,k_z)=i\cos(k_y y)\sin(k_z z)(\cos(k_x x)+i\sin(k_x x)) \qquad (8).$$

Figure 8A:
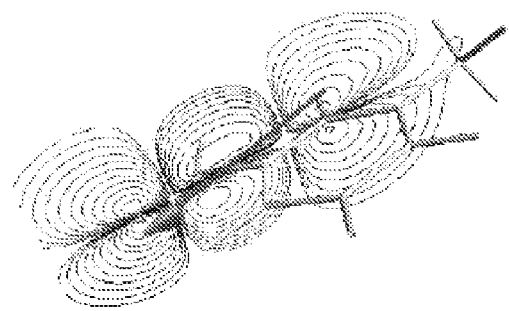
FIG. 8A illustrates one example of a projection of exemplary half-wavevectors that are 'in phase' with a LUMO of 2-, 3-, and 4-nitrotoluene.
Figure 8B:
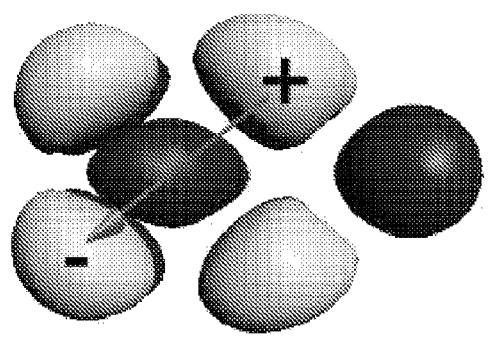
FIG. 8B illustrates another example of a projection of exemplary half-wavevectors of FIG. 8A onto an xy-plane of 4-nitrotoluene.
Figure 8B:
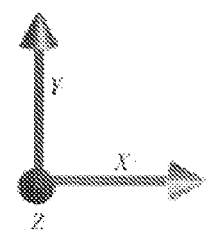
Figure 8C:
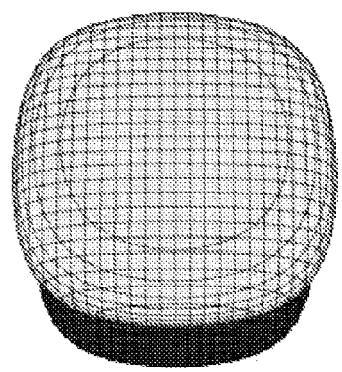
FIG. 8C illustrates one example of a wavefunction corresponding to the wavevector of FIG. 8B.

In this example, the reflection symmetry in the xz and yz-planes requires the center of a captured electron's wavefunction to sit on the x-axis. There is only one set of wavevectors that simultaneously satisfy this constraint and connect regions of opposite phase. FIG. 8A illustrates example half-wavevectors that are "in phase" with the LUMOs of 2-, 3-, and 4-nitrotoluene projected onto the plane normal to the ring including a nitro oxygen and the carbon at position 2 relative to the nitro group. FIG. 8B illustrates another exemplary projection of this wavevector onto the xy-plane of 4-nitrotoluene. FIG. 8C illustrates an exemplary wavefunction corresponding to this wavevector. In this example, the wavefunction is centered on the molecular x-axis for 3 and 4 nitrotoluene and experiences both positive and negative overlap with the LUMO of FIG. 8A.

FIGS. 8A to 8C illustrate the projection of the wavevectors in two planes along with the real component of the wavefunction of equation (8). Though these displacement vectors are of a length expected for half the wavelength of 1.0 eV electron ($\approx$12 Å), the intervening region of opposite phase leads to significant cancellations between the wavefunctions of the incoming electron and the LUMO. The observed weak resonance at about 1.0 eV is consistent with the predicted data.

Figure 9:
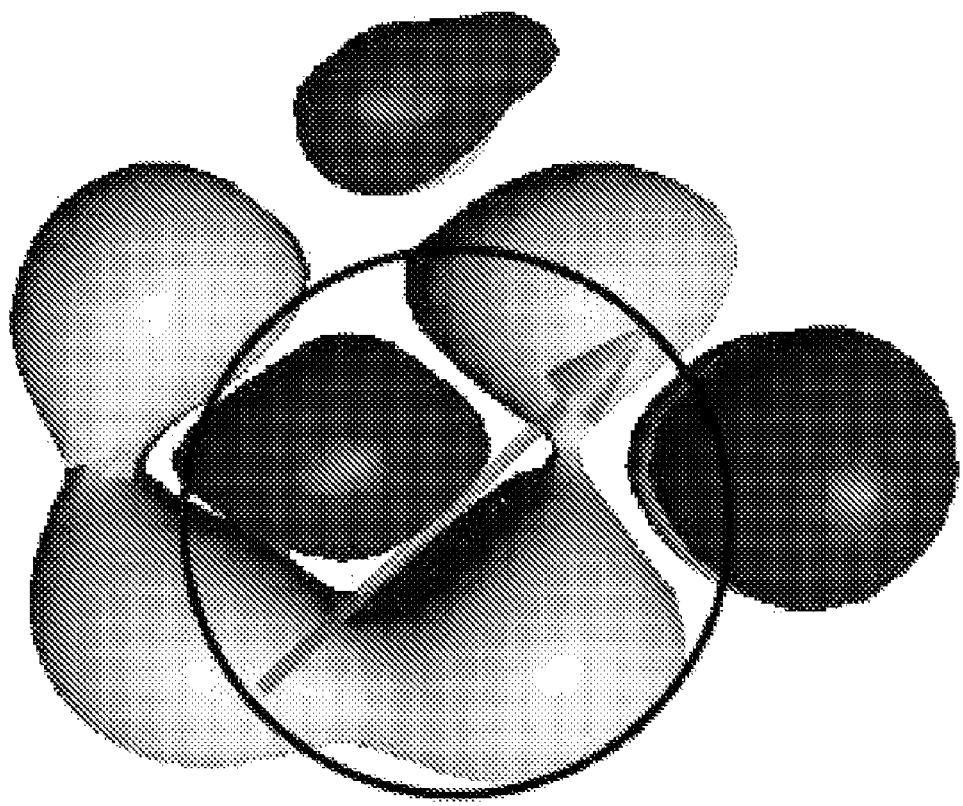
FIG. 9 illustrates local symmetry of 2-nitrotoluene as $C_h$.

The symmetry reduction seen in the LUMO of the 2-nitrotoluene removes one of the constraints on the incident electron wavevector, confining its center only to the xy-plane. No longer tethered to the x-axis, a new family of wavevectors (e.g., also $\approx$12 Å in length) contributes to the reaction rate. The projection of these wavevectors in the xy-plane is shown in FIG. 9. Because the center of these vectors has been displaced to a region of low LUMO amplitude, the cancellation will be reduced over those of 3- and 4-nitrotoluene, leading to a more pronounced 1.0 eV resonance. This theoretical calculation is consistent with experimental observation.

In this example involving nitrated aromatic compounds, all first principle calculations have been conducted using the Amsterdam Density Functional code. The correction to the exchange and correlation specified by Perdew-Wang were used for all calculations. Triple zeta and double zeta basis sets including polarization terms were used. The symmetry arguments presented here were not altered by the choice of basis set.

It is to be noted that the aspects and embodiments described herein may be conveniently implemented using one or more machines (e.g., a general purpose computing device) programmed according to the teachings of the present specification, as will be apparent to those of ordinary skill in the computer art. For example, various aspects of a method approximating a electron resonance spectra data for a chemical constituent, such as method 200, may be implemented as machine-executable instructions (i.e., software coding), such as program modules executed by one or more machines. Typically a program module may include routines, programs, objects, components, data structures, etc. that perform specific tasks. Appropriate machine-executable instructions can readily be prepared by skilled programmers based on the teachings of the present disclosure, as will be apparent to those of ordinary skill in the software art.

Such software may be a computer program product that employs a machine-readable medium. A machine-readable medium may be any medium that is capable of storing and/or encoding a sequence of instructions for execution by a machine (e.g., a general purpose computing device) and that causes the machine to perform any one of the methodologies and/or embodiments described herein. Examples of a machine-readable medium include, but are not limited to, a magnetic disk (e.g., a conventional floppy disk, a hard drive disk), an optical disk (e.g., a compact disk "CD", such as a readable, writeable, and/or re-writable CD; a digital video disk "DVD", such as a readable, writeable, and/or rewritable DVD), a magneto-optical disk, a read-only memory "ROM" device, a random access memory "RAM" device, a magnetic card, an optical card, a solid-state memory device (e.g., a flash memory), an EPROM, an EEPROM, and any combinations thereof. A machine-readable medium, as used herein, is intended to include a single medium as well as a collection of physically separate media, such as, for example, a collection of compact disks or one or more hard disk drives in combination with a computer memory. In one example, a machine-readable medium having instructions for implementing one or more aspects and/or embodiments as disclosed herein may be associated with and/or part of an spectrographic analytical device, such as an EM/MS.

Examples of a computing device include, but are not limited to, a computer workstation, a terminal computer, a server computer, a handheld device (e.g., tablet computer, a personal digital assistant "PDA", a mobile telephone, etc.), a web appliance, a network router, a network switch, a network bridge, any machine capable of executing a sequence of instructions that specify an action to be taken by that machine, and any combinations thereof. In one example, a general purpose computing device may include and/or be included in, a kiosk.

Figure 10:
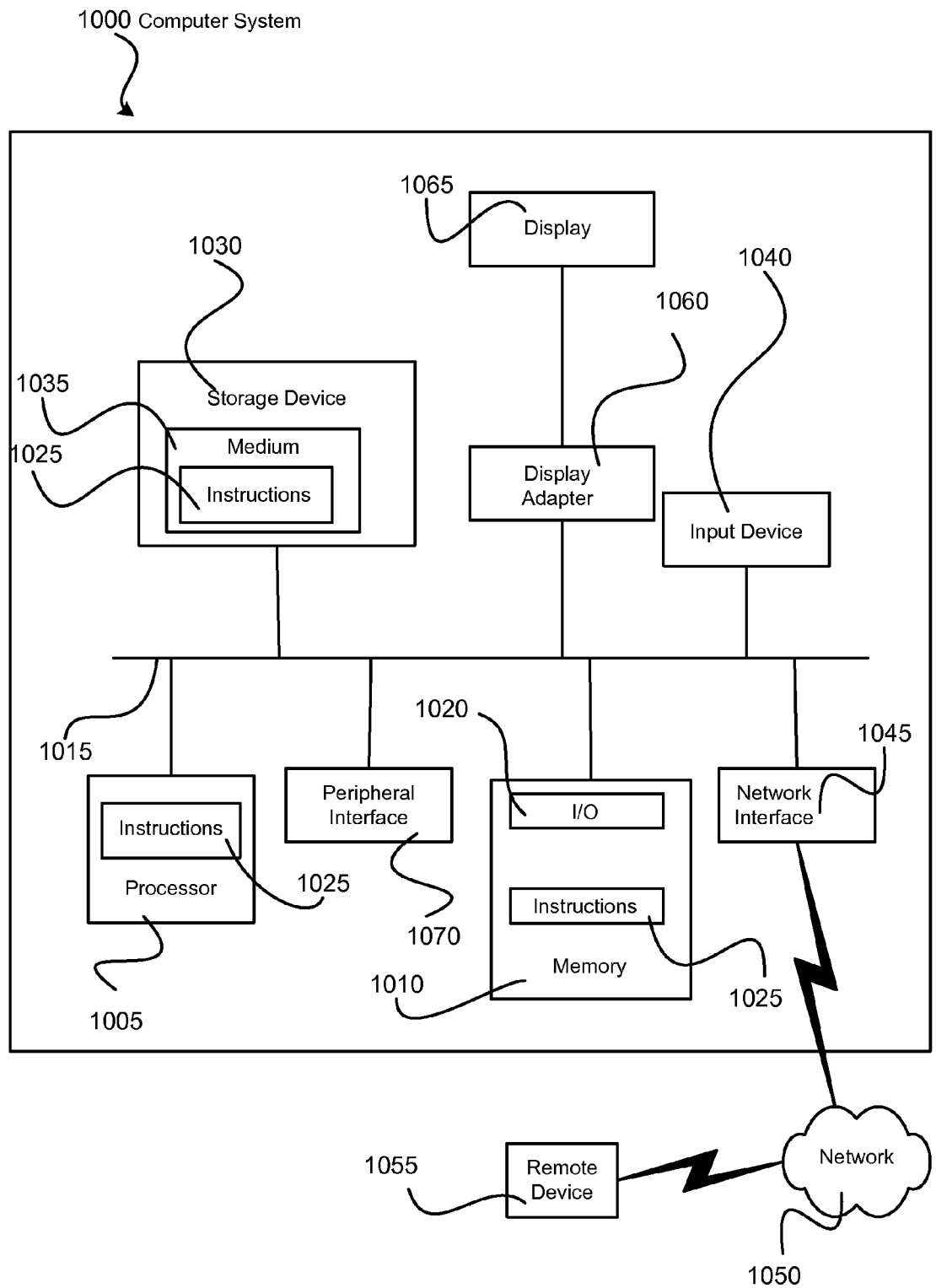
FIG. 10 illustrates one embodiment of a computing device.

FIG. 10 shows a diagrammatic representation of one embodiment of a computing device in the exemplary form of a computer system 1000 within which a set of instructions for causing the device to perform any one or more of the aspects and/or methodologies of the present disclosure may be executed. Computer system 1000 includes a processor 1005 and a memory 1010 that communicate with each other, and with other components, via a bus 1015. Bus 1015 may include any of several types of bus structures including, but not limited to, a memory bus, a memory controller, a peripheral bus, a local bus, and any combinations thereof, using any of a variety of bus architectures.

Memory 1010 may include various components (e.g., machine readable media) including, but not limited to, a random access memory component (e.g., a static RAM "SRAM", a dynamic RAM "DRAM", etc.), a read only component, and any combinations thereof. In one example, a basic input/output system 1020 (BIOS), including basic routines that help to transfer information between elements within computer system 1000, such as during start-up, may be stored in memory 1010. Memory 1010 may also include (e.g., stored on one or more machine-readable media) instructions (e.g., software) 1025 embodying any one or more of the aspects and/or methodologies of the present disclosure. In another example, memory 1010 may further include any number of program modules including, but not limited to, an operating system, one or more application programs, other program modules, program data, and any combinations thereof.

Computer system 1000 may also include a storage device 1030. Examples of a storage device (e.g., storage device 1030) include, but are not limited to, a hard disk drive for reading from and/or writing to a hard disk, a magnetic disk drive for reading from and/or writing to a removable magnetic disk, an optical disk drive for reading from and/or writing to an optical media (e.g., a CD, a DVD, etc.), a solid-state memory device, and any combinations thereof. Storage device 1030 may be connected to bus 1015 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1030 may be removably interfaced with computer system 1000 (e.g., via an external port connector (not shown)). Particularly, storage device 1030 and an associated machine-readable medium 1035 may provide nonvolatile and/or volatile storage of machine-readable instructions, data structures, program modules, and/or other data for computer system 1000. In one example, software 1025 may reside, completely or partially, within machine-readable medium 1035. In another example, software 1025 may reside, completely or partially, within processor 1005.

Computer system 1000 may also include an input device 1040. In one example, a user of computer system 1000 may enter commands and/or other information into computer system 1000 via input device 1040. Examples of an input device 1040 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), touchscreen, and any combinations thereof. Input device 1040 may be interfaced to bus 1015 via any of a variety of interfaces (not shown) including, but not limited to, a serial interface, a parallel interface, a game port, a USB interface, a FIREWIRE interface, a direct interface to bus 1015, and any combinations thereof.

A user may also input commands and/or other information to computer system 1000 via storage device 1030 (e.g., a removable disk drive, a flash drive, etc.) and/or a network interface device 1045. A network interface device, such as network interface device 1045 may be utilized for connecting computer system 1000 to one or more of a variety of networks, such as network 1050, and one or more remote devices 1055 connected thereto. Examples of a network interface device include, but are not limited to, a network interface card, a modem, and any combination thereof. Examples of a network or network segment include, but are not limited to, a wide area network (e.g., the Internet, an enterprise network), a local area network (e.g., a network associated with an office, a building, a campus or other relatively small geographic space), a telephone network, a direct connection between two computing devices, and any combinations thereof. A network, such as network 1050, may employ a wired and/or a wireless mode of communication. In general, any network topology may be used. Information (e.g., data, software 1025, etc.) may be communicated to and/or from computer system 1000 via network interface device 1045.

Computer system 1000 may further include a video display adapter 1060 for communicating a displayable image to a display device, such as display device 1065. Examples of a display device include, but are not limited to, a liquid crystal display (LCD), a cathode ray tube (CRT), a plasma display, and any combinations thereof. In addition to a display device, a computer system 1000 may include one or more other peripheral output devices including, but not limited to, an audio speaker, a printer, and any combinations thereof. Such peripheral output devices may be connected to bus 1015 via a peripheral interface 1070. Examples of a peripheral interface include, but are not limited to, a serial port, a USB connection, a FIREWIRE connection, a parallel connection, and any combinations thereof.

A digitizer (not shown) and an accompanying pen/stylus, if needed, may be included in order to digitally capture freehand input. A pen digitizer may be separately configured or coextensive with a display area of display device 1065. Accordingly, a digitizer may be integrated with display device 1065, or may exist as a separate device overlaying or otherwise appended to display device 1065.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of calculating an electron resonance spectra data value for each of one or more chemical constituents, the method comprising:
   identifying one or more potential electron capture orbitals for each of the one or more chemical constituents;
   determining an electron orbital wavefunction for each of the one or more potential electron capture orbitals; and
   generating a theoretical electron resonance spectra data value for each of the one or more chemical constituents from the corresponding electron orbital wavefunctions.

2. A method according to claim 1, wherein at least one of the theoretical electron resonance spectra data values includes a data value selected from the group consisting of a fragmentation probability value, a reaction rate for electron capture, an electron resonance spectrum, an electron resonance energy value, a relative electron energy peak intensity value, a relative electron energy peak width, and any combinations thereof.

3. A method according to claim 1, wherein at least one of the theoretical electron resonance spectra data values includes an electron resonance spectrum.

4. A method according to claim 1, wherein at least on of the one or more chemical constituents is a nitrated aromatic compound.

5. A method according to claim 1, wherein said identifying one or more potential electron capture orbitals includes identifying one or more π-orbitals.

6. A method according to claim 1, wherein one or more candidates for the one or more potential electron capture orbitals is determined by a process including:
   measuring an electron resonance spectrum for each of a plurality of compounds of a group of compounds having a similar structure with variance of one or more functional groups;
   identifying one or more patterns in spectral peak shifting as a function of the variance of the one or more functional groups; and
   identifying one or more unoccupied molecular orbitals having a symmetry that is consistent with the one or more patterns and that are most likely to capture an electron.

7. A method according to claim 1, wherein said generating a theoretical electron resonance spectra data value includes:
   determining a Fourier Transform of each of the electron orbital wavefunctions; and
   averaging the Fourier Transform of each of the electron orbital wavefunctions over all wave vectors of the Fourier Transform while keeping overall wave vector magnitude fixed.

8. A method according to claim 1, wherein said generating a theoretical electron resonance spectra data value includes applying the Fourier Transform of each of the electron orbital wavefunctions to the following equation:

$$\Gamma = \frac{V_0^2}{2\hbar\Omega} \int \frac{d^3\vec{K}d\Omega_k}{(2\pi)^3} |\phi(\vec{k})|^2 \delta(\varepsilon_k + \varepsilon_\phi - E_K - \Delta)$$

where k is an incident wave vector of the electron, φ(k) is the Fourier Transform of a capturing molecular orbital wavefunction of a core of the chemical constituent, $V_0$ is a repulsive constant, $\varepsilon_k$ is a kinetic energy of the incident electron, $E_K$ is a final fragment kinetic energy, $\varepsilon_\phi$ is an electron binding energy for the capturing orbital, Q is a volume of a box used to normalize the continuum eigenstates, and Δ is a binding energy of the fragment to the core.

9. A method according to claim 1, wherein the steps of the method of claim 1 are repeated for each of a plurality of isomers of a chemical constituent to generate a theoretical electron resonance spectra data value for each of the plurality of isomers.

10. A method according to claim 1, further comprising building an electron resonance spectra data value library from the theoretical electron resonance spectra data value of each of the one or more chemical constituents.

11. A method according to claim 1, further comprising:
   measuring an experimental electron resonance spectra data value for an unknown chemical constituent; and
   comparing the experimental electron resonance spectra data value with the theoretical electron resonance spectra data value to identify the unknown chemical constituent.

12. A method according to claim 11, wherein said measuring step includes the use of an electron monochromator-mass spectrometer.

13. A method according to claim 11, further comprising experimentally determining a class of chemical constituents to which the unknown chemical constituent belongs using mass spectrometry; and said comparing step includes identifying the unknown chemical constituent as an isomer of the class of chemical constituents.

14. A method according to claim 11, wherein said comparing step includes comparing a resonance energy, a normalized peak intensity, and/or a resonance energy peak width.

15. A method according to claim 1, wherein at least one of the electron orbital wavefunctions is an excited state wavefunction.

16. A method according to claim 1, wherein at least one of the electron orbital wavefunctions is a ground state wavefunction.

17. A method according to claim 1, further comprising displaying the theoretical fragmentation probability value.

18. A computer readable medium including one or more theoretical electron resonance spectra data values according to claim 1.

19. An electron monochromator-mass spectrometer analytical device including a computer readable medium according to claim 18.

20. A computer readable medium containing computer executable instructions implementing a method of calculating an electron resonance spectra data value for each of one or more chemical constituents, the instructions comprising:
   a set of instructions for identifying one or more potential electron capture orbitals for each of the one or more chemical constituents;
   a set of instructions for determining an electron orbital wavefunction for each of the one or more potential electron capture orbitals; and
   a set of instructions for generating a theoretical electron resonance spectra data value for each of the one or more chemical constituents from the corresponding electron orbital wavefunctions.

21. A computer readable medium according to claim 20, wherein at least one of the theoretical electron resonance spectra data values includes a data value selected from the group consisting of a fragmentation probability value, a reaction rate for electron capture, an electron resonance spectrum, an electron resonance energy value, a relative electron energy peak intensity value, relative electron energy peak width, and any combinations thereof.

22. A computer readable medium according to claim 20, wherein said set of instructions for generating a theoretical electron resonance spectra data value includes:
   a set of instructions for determining a Fourier Transform of each of the electron orbital wavefunctions; and
   a set of instructions for averaging the Fourier Transform of each of the electron orbital wavefunctions over all wave vectors of the Fourier Transform while keeping overall wave vector magnitude fixed.

23. A computer readable medium according to claim 20, wherein said set of instructions for generating a theoretical electron resonance spectra data value includes a set of instructions for applying the Fourier Transform of each of the electron orbital wavefunctions to the following equation:

$$\Gamma = \frac{V_0^2}{2\hbar\Omega} \int \frac{d^3\vec{K}d\Omega_k}{(2\pi)^3} |\phi(\vec{k})|^2 \delta(\varepsilon_k + \varepsilon_\phi - E_K - \Delta)$$

where k is an incident wave vector of the electron, φ(k) is the Fourier Transform of a capturing molecular orbital wavefunction, $V_0$ is a repulsive constant, $\varepsilon_k$ is a kinetic energy of the incident electron, $E_K$ is a final fragment kinetic energy, $\varepsilon_\phi$ is an electron binding energy for the capturing orbital, Ω is a volume of a box used to normalize the continuum eigenstates, and $\Delta$ is a binding energy of the fragment to the core.

24. A computer readable medium according to claim 20, further comprising:
   a set of instructions for measuring an experimental electron resonance spectra data value for an unknown chemical constituent; and
   a set of instructions for comparing the experimental electron resonance spectra data value with the theoretical electron resonance spectra data value to identify the unknown chemical constituent.

25. A system for calculating an electron resonance spectra data value for each of one or more chemical constituents, the system comprising:
   means for identifying one or more potential electron capture orbitals for each of the one or more chemical constituents;
   means for determining an electron orbital wavefunction for each of the one or more potential electron capture orbitals; and
   means for generating a theoretical electron resonance spectra data value for each of the one or more chemical constituents from the corresponding electron orbital wavefunctions.

26. A system according to claim 25, wherein at least one of the theoretical electron resonance spectra data values includes a data value selected from the group consisting of a fragmentation probability value, a reaction rate for electron capture, an electron resonance spectrum, an electron resonance energy value, a relative electron energy peak intensity value, relative electron energy peak width, and any combinations thereof.

27. A system according to claim 25, wherein said set of instructions for generating a theoretical electron resonance spectra data value includes:

means for determining a Fourier Transform of each of the electron orbital wavefunctions; and
   means for averaging the Fourier Transform of each of the electron orbital wavefunctions over all wave vectors of the Fourier Transform while keeping overall wave vector magnitude fixed.

28. A system according to claim 25, wherein said set of instructions for generating a theoretical electron resonance spectra data value includes a means for applying the Fourier Transform of each of the electron orbital wavefunctions to the following equation:

$$\Gamma = \frac{V_0^2}{2\hbar\Omega} \int \frac{d^3\vec{K} d\Omega_k}{(2\pi)^3} |\phi(\vec{k})|^2 \delta(\varepsilon_k + \varepsilon_\phi - E_K - \Delta)$$

where k is an incident wave vector of the electron, $\phi(k)$ is the Fourier Transform of a capturing molecular orbital wavefunction, $V_0$ is a repulsive constant, $\epsilon_k$ is a kinetic energy of the incident electron, $E_K$ is a final fragment kinetic energy, $\epsilon_\phi$ is an electron binding energy for the capturing orbital, $\Omega$ is a volume of a box used to normalize the continuum eigenstates, and $\Delta$ is a binding energy of the fragment to the core.

29. A system according to claim 25, further comprising:
   means for measuring an experimental electron resonance spectra data value for an unknown chemical constituent; and
   means for comparing the experimental electron resonance spectra data value with the theoretical electron resonance spectra data value to identify the unknown chemical constituent.

* * * * *

UNITED STATES PATENT AND TRADEMARK OFFICE
CERTIFICATE OF CORRECTION

PATENT NO. : 7,570,055 B1  
APPLICATION NO. : 11/689497  
DATED : August 4, 2009  
INVENTOR(S) : Clougherty et al.

Page 1 of 1

It is certified that error appears in the above-identified patent and that said Letters Patent is hereby corrected as shown below:

In column 14, line 65, delete "on" and insert -- one -- therefore; and

In column 15, line 41, delete "Q" and insert -- Ω -- therefore.

Signed and Sealed this

Seventeenth Day of November, 2009

David J. Kappos  
*Director of the United States Patent and Trademark Office*